(12) United States Patent
Aarts

(10) Patent No.: US 8,260,405 B2
(45) Date of Patent: Sep. 4, 2012

(54) MONITORING APPARATUS FOR MONITORING A USER'S HEART RATE AND/OR HEART RATE VARIATION; WRISTWATCH COMPRISING SUCH A MONITORING APPARATUS

(75) Inventor: Ronaldus Maria Aarts, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 820 days.

(21) Appl. No.: 12/097,764

(22) PCT Filed: Dec. 11, 2006

(86) PCT No.: PCT/IB2006/054734
§ 371 (c)(1),
(2), (4) Date: Jun. 17, 2008

(87) PCT Pub. No.: WO2007/072288
PCT Pub. Date: Jun. 28, 2007

(65) Prior Publication Data
US 2008/0262364 A1 Oct. 23, 2008

(30) Foreign Application Priority Data
Dec. 19, 2005 (EP) .................... 05 112425

(51) Int. Cl.
*A61N 5/04* (2006.01)
*A61N 5/02* (2006.01)

(52) U.S. Cl. ........ 600/509; 600/377; 600/508; 600/481; 600/483

(58) Field of Classification Search ................. 600/377, 600/508, 481, 483
See application file for complete search history.

(56) References Cited

U.S. PATENT DOCUMENTS

| | | | |
|---|---|---|---|
| 3,838,684 A | 10/1974 | Manuel et al. | |
| 3,841,315 A | 10/1974 | Kopp | |
| 4,466,289 A | 8/1984 | Lam | |
| 5,002,061 A | 3/1991 | Close et al. | |
| 6,295,466 B1 * | 9/2001 | Ishikawa et al. | 600/509 |
| 6,491,647 B1 | 12/2002 | Bridger et al. | |
| 6,616,612 B1 * | 9/2003 | Nissila et al. | 600/485 |
| 2004/0039254 A1 | 2/2004 | Stivoric et al. | |
| 2004/0220485 A1 * | 11/2004 | Rytky | 600/509 |
| 2004/0243005 A1 * | 12/2004 | Rapps | 600/481 |
| 2005/0171443 A1 | 8/2005 | Gorenberg et al. | |

FOREIGN PATENT DOCUMENTS

| | | |
|---|---|---|
| EP | 1034736 | 9/2000 |
| WO | W00102049 | 1/2001 |

* cited by examiner

*Primary Examiner* — Nicole F Lavert

(57) ABSTRACT

A monitoring apparatus (4) monitors a user's heart rate and/or heart rate variation. The apparatus includes a capacitor (22) which is positionable on or near a body part of a person, for example a person's limb, for example an arm (3), such that an electrical capacitance of the capacitor (22) is influenced by blood pressure pulses of blood running through the body part. The apparatus (4) also includes a data processor (26) for determining the heart rate and/or heart rate variation from changes in the capacitance of the capacitor (22).

21 Claims, 3 Drawing Sheets

40

MONITORING APPARATUS FOR MONITORING A USER'S HEART RATE AND/OR HEART RATE VARIATION; WRISTWATCH COMPRISING SUCH A MONITORING APPARATUS

FIELD OF THE INVENTION

The invention relates to a monitoring apparatus for monitoring a user's heart rate and/or heart rate variation.

Apparatuses for monitoring a user's heart rate and/or heart rate variation generally have a medical use, such as for determining the occurrence of a heart failure and/or the possibility of occurrence a heart failure.

Also such apparatuses are used by athletes, for example in a training scheme.

BACKGROUND OF THE INVENTION

A monitoring apparatus is known from American patent specification U.S. Pat. No. 3,838,684. The monitoring apparatus comprises a pressure sensitive sensor, which during use abuts a part of a skin surface for measuring the heart rate. The pressure pulses obtained by the sensor are converted to an electrical pulse. Furthermore, a light source is provided which allows a user to count the light pulses representative of each heart beat during a 15 second interval to thereby determine visually what his heart rate is at any given time. The apparatus is compact and strapped about the wrist.

A disadvantage of the known monitoring apparatus is its unreliability, because in order to obtain good heart rate measurements, the pressure sensor is required to be located exactly on a position adjacent to a blood vessel from which the measurements are to be obtained. Therefore, the apparatus is not suitable for use by athletes who prefer to use the apparatus while running, jumping and/or moving in any other manner.

SUMMARY OF THE INVENTION

An object of the present invention is to address the disadvantages mentioned above.

According to the present invention, a monitoring apparatus for monitoring a user's heart rate and/or heart rate variation, the apparatus comprising: a capacitor having at least two capacitor electrodes, wherein the capacitor electrodes are position able adjacent to different surface parts of a body part of a person, the body part being for example a person's limb, for example an arm, such that an electrical capacitance of the capacitor is influenced by blood pressure pulses of blood running through the body part, wherein the apparatus further comprises a data processor for determining the heart rate and/or heart rate variation from changes in the capacitance of the capacitor.

Surprisingly, it is possible to measure a person's heart beat by using a capacitor having capacitor electrodes which are located adjacent to different surface parts the person's body part. As a result of the pressure pulses running through the blood vessel, the capacitance is influenced. Due to capacity changes it is possible to determine the occurrence of heartbeats.

Preferably, in order to obtain accurate measurements, the different surfaces are located at substantially opposite sides of the person's body part, particularly such that the body part extends between the electrodes during use.

In order to facilitate the possibility for a user to read measurements of his own heart rate, a preferred embodiment of the apparatus comprises an output device for auditively and/or visually making knowable to the user the heart rate and/or heart rate variation determined by the data processor.

In an embodiment of the apparatus according to the present invention, the apparatus comprises an oscillator for sending an oscillating signal through the capacitor to be able adequately determines capacity changes.

Preferably the oscillator is arranged to generate a binary signal. An advantage of a binary signal is that in the data processor no further A/D-converter is necessary.

To be able to determine changes in frequency, the data processor of a further embodiment of the apparatus according to the present invention comprises a one shot unit for generating a pulse train, wherein the pulse train is formed by pulses generated by the one shot unit in response to an up going flank or a down going flank in the oscillating signal. In such an embodiment, the data processor may comprise an averaging unit for generating a moving average of the pulse train, the moving average being indicative of a frequency changes of the oscillating signal.

In an advanced embodiment of the apparatus according to the present invention an accelerometer is provided for determining acceleration of the body part. If the acceleration of body part is known while monitoring the heart rate and/or heart rate variation, it is possible to compensate for any interference and/or disturbance occurring as a result of the acceleration.

To suitably implement the compensation for the interference or the disturbance, the data processor can be arranged for determining an estimation of a disturbance value in measurements which value has been caused by the acceleration of the limb.

A basic idea of the present invention is to use only a single wristband, particularly a wristwatch, having simple means to monitor the user's heart, without using for example a chest band. Herein, preferably, the single wristband comprising the capacitor having the at least two capacitor electrodes preferably also comprises the data processor, and more particularly also comprises the output device These and other aspects of the invention will be apparent from and elucidated with reference to the embodiment described hereinafter with reference to the accompanying drawing, wherein same reference signs refer to corresponding reference parts.

DESCRIPTION OF PREFERRED EMBODIMENTS

Figure 1:
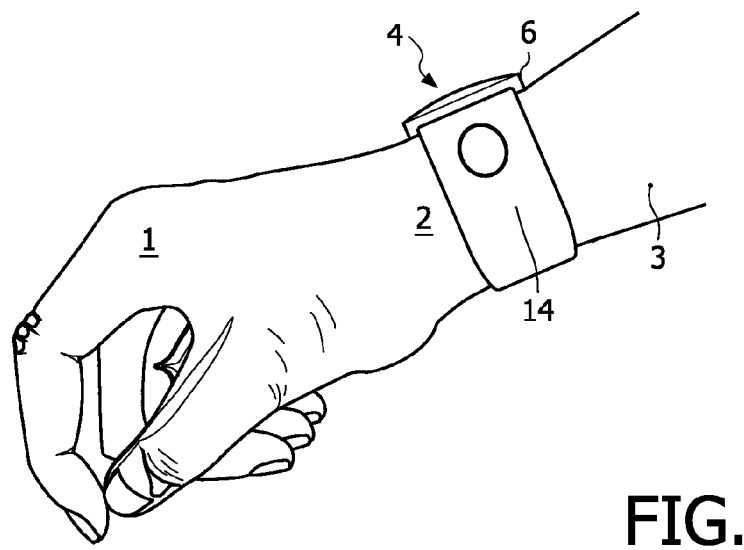
FIG. 1 is a perspective view of a first embodiment of the apparatus according to the present invention.
Figure 2:
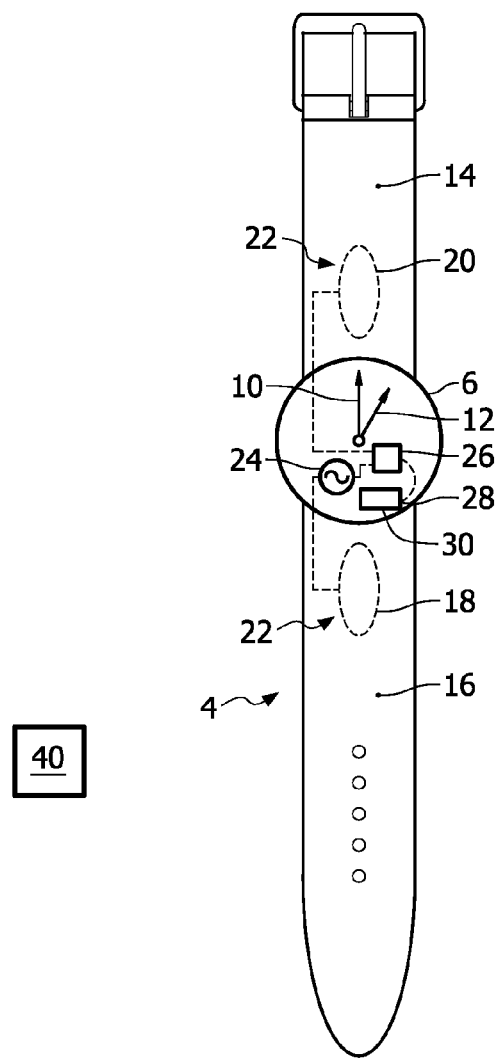
FIG. 2 is a top view of the apparatus shown in FIG. 1.

FIG. 1 shows a hand 1 and a wrist 2 of an arm 3 of a person who is using a first embodiment of a monitoring apparatus 4. Referring to FIG. 2, the apparatus 4 comprises a housing 6 having a time display 8 with two pointers 10 and 12, and a wrist band having a first strap part 14 and a second strap part 16. The apparatus is configured to provide an electrical capacitor 22, having electrodes 18, 20. Each of the strap parts 14, 16 is provided with a capacitor electrode 18, 20 in the form of a plate 18, 20, together forming the capacitor 22 during use, when the apparatus is carried by a user. The capacitor plates can be positioned adjacent to different surface parts. In the embodiments shown, the surface parts are located on substantially opposite sides of the arm 3 when in use, that is, on sides of arm 3 that are substantially faced away from each other.

The electrodes 18 and 20 are electrically coupled to an oscillator 24, which, in operation, sends a periodic, electrical signal through the capacitor 22. The apparatus 4 further comprises a data processor 26 for determining the heart rate and/or heart rate variation from changes in the capacitance of the capacitor. Also, the apparatus 4 comprises an output device 28 for auditively and/or visually making knowable to the user the heart rate and/or heart rate variation determined by the data processor 26. In FIG. 2, the output device 28 is formed by a visual display 30.

Figure 3:
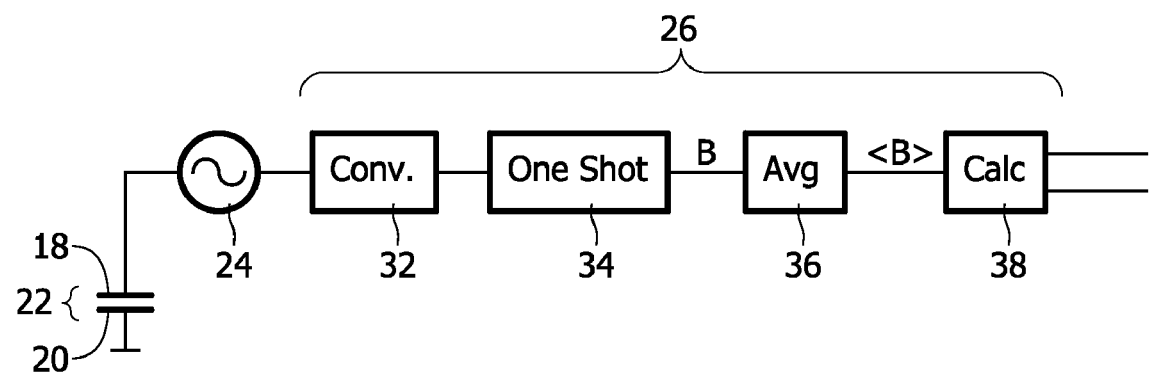
FIG. 3 is a schematic of a data processor, as comprised in the apparatus of FIGS. 1 and 2.

The data processor 26 preferably comprises a frequency detector. Many kinds of frequency detectors are suitable for use in the data processor 26. However, in this specific embodiment (see FIG. 3), frequency detector of the data processor 26 of the apparatus 4 comprises a converter 32 for converting the periodic signal to a binary signal. In this specific embodiment the converter is a comparator with an output which is a logical one if the input is >0 and which output is a logical zero if the input is <0. However, other kinds of suitable converters may be employed. The frequency detector further comprises a one shot unit 34 for generating a pulse train B as an exit signal in response to a change in signal value of the binary signal and an averaging unit 36 for generating a moving average <B> of the pulse train B generated by the one shot unit 34. In order to avoid the necessity of the converter 32 an oscillator can be provided arranged to generate a binary signal, such as a block signal. As a single pulse generated by the one shot unit 34 has a fixed time length and the pulse is generated only in response to a change in the signal value of the exit signal, the moving average value generated by the averaging unit 36 is indicative of the frequency of the binary signal. Based on this moving average signal, the calculating unit 38 can calculate the heart rate and/or heart rate variations.

An athlete using the apparatus 4 which, in this embodiment, is incorporated in a wrist watch, can, for instance while running, easily check his heart rate and/or variations therein by looking at his watch. If the heart rate becomes too high, the athlete can lower his effort in order to maintain a predetermined training scheme.

Alternatively, the apparatus 4 may be used while playing computer games. The heart rate and/or heart rate variations may be used as a parameter in computer games. The abilities of a computer game character to be controlled by the user of the apparatus may, for instance, be influenced by the heart rate of the user.

Another application is use of the apparatus, wherein the heart rate and/or heart rate variations are used to determine the occurrence of a heart failure and/or the possibility of occurrence of a heart failure. Upon the determination of a heart failure, the apparatus can be arranged to generate an alarm signal to an external receiver 40.

Figure 4:
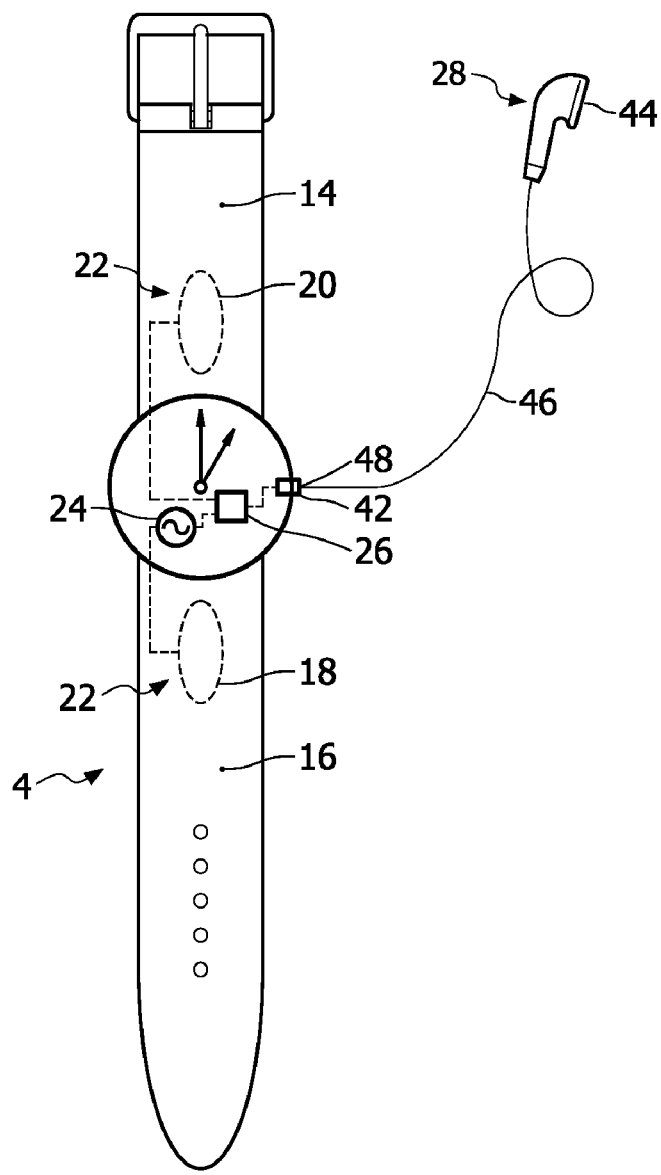
FIG. 4 is a top view of a modification of the apparatus shown in FIGS. 1 and 2.

A modification of the first embodiment is shown in FIG. 4 in which an output device 28 is provided for auditively making knowable to the person the heart rate and/or heart rate variation. Instead of being formed by the visual display 30, the output device 28 is formed by a socket 42 and an earpiece 44 having a wiring 46 and a plug 48, which is arranged to be inserted in the socket 42. In the modification of the first embodiment, the data processor 26 is arranged to periodically notify the person of his/her heart rate and/or heart rate variations by using sound, for instance a human voice. However, instead using the wiring 46 and the plug 48, the earpiece 44 and the output device 28 may also be arranged to communicate in a wireless manner.

Figure 5:
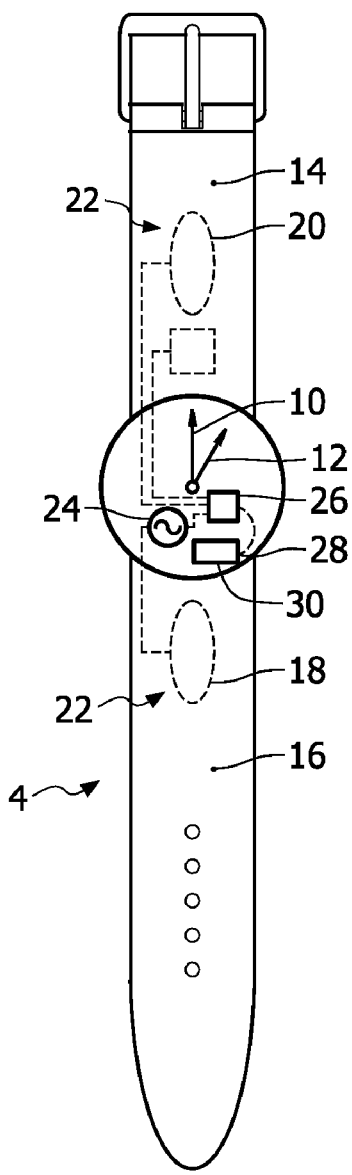
FIG. 5 is a top view of a second embodiment of the apparatus according to the present invention.

FIG. 5 schematically shows a second, more advanced embodiment of the apparatus. The second embodiment of the apparatus is similar to the first embodiment. However, in FIG. 5 it can be seen that the second embodiment of the apparatus also comprises an accelerometer 50 for determining acceleration of the arm 3. The accelerometer 50 determines an acceleration value of the arm 3. The data processor 26 is suitably arranged for determining an estimation of a disturbance value in measurements in the at least one electrical parameter caused by the acceleration of the arm in order to be able to compensate for this disturbance. Furthermore, the accelerometer 50 may be arranged to recognize periodic patterns in the acceleration of the arm in order to even further increase the ability to compensate for the disturbance.

It will be clear to a person skilled in the art that the invention is not limited to the embodiments shown above. For instance, various data processors in addition to the data processors disclosed herein may be suitable for application without departing from the scope of the present invention as determined by the accompanying claims.

For example, a mentioned wristband can be configured in various ways, and can include for example one or more straps, and/or be arranged in a different way. Also, a mentioned capacitor, data processor, and/or output device can be coupled to a wristband in various ways, For example, the capacitor, data processor, and/or output device can be coupled to the wristband can be integrally connected to the wristband, can be detachably connectable thereto, be at least partly comprised in a housing of the wristband, and/or in a different manner. Also, the heart rate and/or heart rate variation may be stored in a memory comprised in, for instance, the data processor. Such embodiments are within the scope of the present invention as determined by the accompanying claims.

Owing to the invention, it is possible to easily measure a person's heart beat by using a capacitor in an unconventional manner.

It is noted that the word "comprising" does not exclude the presence other elements in an part of the apparatus or additional steps in a method. It is also noted that the word "a"/"an" does not exclude plurality. Furthermore, the reference signs in the claims are not to be construed as to limit the scope of the present invention.

The invention claimed is:

1. A monitoring apparatus for monitoring a user's heart rate and/or heart rate variation, the apparatus comprising:
   an oscillator which generates an oscillating signal;
   first and second capacitor electrodes, the first electrode is connected to said oscillator, the capacitor electrodes being arranged to be mounted to capacitively couple with different surface parts of a blood carrying body part of a person, such that an electrical capacitance between the electrodes across the body part between the electrodes changes in response to blood pressure pulses of blood running through the capacitively coupled body part;
   a data processor connected to said oscillator and said second electrode, the processor being programmed to determine a heart rate or heart rate variation from changes in the capacitance of the capacitively coupled electrodes and body part; and an output device connected to the processor to provide an auditory and/or visual output indicative of the heart rate or the heart rate variation.

2. The apparatus according to claim 1, wherein the oscillator is arranged to generate a binary signal.

3. The apparatus according to claim 1, wherein the data processor comprises a frequency detector arranged to determine frequency changes.

4. The apparatus according to claim 1, wherein the data processor comprises a one shot unit which generates a pulse train, the pulse train being formed by pulses generated by the one shot unit in response to an up going flank or a down going flank in the oscillating signal.

5. The apparatus according to claim 4, wherein the data processor comprises an averaging unit for generating a moving average of the pulse train, the moving average being indicative of a frequency changes of the oscillating signal.

6. The apparatus according to claim 1, the different surface parts being located at substantially opposite sides of the person's body part, particularly such that the body part extends between the electrodes during use and changes in blood volume in the body part during each heart beat changes the capacitive coupling of the electrodes.

7. The apparatus according to claim 1, wherein the apparatus is provided with a wristband, the wristband supporting the first and second capacitor electrodes in a spaced relationship, and supporting the data processor.

8. A wristband or wrist watch comprising a monitoring apparatus according to claim 1.

9. The apparatus according to claim 1, wherein the heart rate and/or the heart rate variations are used as a parameter in computer games.

10. The apparatus according to claim 1, wherein the heart rate and/or the heart rate variations are used in a training scheme.

11. A method for monitoring a heart of a patient using the apparatus according to claim 1, wherein the heart rate and/or heart rate variations are used to determine the occurrence of a heart failure, wherein, upon the determination of a heart failure, the output device generates an alarm signal.

12. The method according to claim 11, further including: sending the alarm signal to an external receiver.

13. The apparatus according to claim 1, further including: an accelerometer which determines acceleration of the body part.

14. The apparatus according to claim 13, wherein the data processor is further programmed to determine an estimation of a disturbance value in measurements caused by the determined acceleration of the body part and to compensate the determined heart rate or heart rate variation for acceleration of the body part in accordance with the determined estimation of the disturbance value.

15. A method for monitoring a user's heart rate and/or heart rate variation, the method comprising:
sending an oscillating signal between two capacitor electrodes which are adapted to be positioned adjacent to different surface parts of a blood conveying body part of a person, such that an electrical capacitance between the electrodes across a portion of the body part between the electrodes is influenced by blood pressure pulses of blood running through the body part;
determining the heart rate and/or heart rate variation from changes in the capacitance between the electrodes from the oscillating signal; and
with an output device outputting an auditory and/or visual representation of the heart rate and/or the heart rate variation.

16. The method according to claim 15, wherein the electrodes are adapted to be positioned such that the blood conveying body part is at least partly located between the electrodes to function as a dielectric between the electrodes, such that the capacitance varies with the heart rate and/or heart rate variation.

17. A monitoring apparatus for monitoring a user's heart rate and/or heart rate variation, the apparatus comprising:
first and second capacitor electrodes mounted on a support structure which is arranged to electrically couple with a body part of a person which undergoes acceleration;
an accelerometer mounted on the support structure which accelerometer is arranged to measure acceleration of the body part;
a processor mounted to the support structure and connected with the capacitor electrodes and the accelerometer, the processor being programmed to:
determine the heart rate and/or the heart rate variation from changes in capacitance across the first and second electrodes, the determined heart rate and/or heart rate variation being disturbed by the acceleration of the body part,
estimate a disturbance value from an output of the accelerometer, the disturbance value being indicative of the disturbance to the heart rate and/or the heart rate variation attributable to the acceleration of the body part, and
compensate the determined heart rate and/or heart rate variation for the acceleration of the body part.

18. The apparatus according to claim 17, where in the support structure includes at least one strap arranged to attach to a wrist of the person, the capacitor electrodes being mounted in a spaced relationship on the at least one strap.

19. The apparatus according to claim 18 further including:
a display device supported by the at least one strap which displays the acceleration compensated heart rate and/or heart rate variation.

20. The apparatus according to claim 17 further including:
an oscillator connected between one of the capacitor electrodes and the processor.

21. The apparatus according to claim 20 further including:
a converter connected with the oscillator configured to convert an oscillating output of the oscillator into a binary pulse train.

* * * * *